(12) United States Patent
Lingelbach et al.

(10) Patent No.: US 11,482,314 B1
(45) Date of Patent: Oct. 25, 2022

(54) PHARMACEUTICAL TRANSPORT SYSTEM INCLUDING RFID BASED LOCK OPERATION AND RELATED METHODS

(71) Applicant: Inmar Rx Solutions, Inc., Ft. Worth, TX (US)

(72) Inventors: Matthew Lingelbach, Clemmons, NC (US); Melissa Bube, High Point, NC (US); Vlad A. Catlan, Winston-Salem, NC (US); Marko Milojevic, Jamestown, NC (US); Jared O. Santibanez, Forney, TX (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 0 days.

(21) Appl. No.: 17/226,809

(22) Filed: Apr. 9, 2021

(51) Int. Cl.
| | | |
|---|---|---|
| *G16H 20/13* | (2018.01) | |
| *G06F 21/31* | (2013.01) | |
| *A61J 1/00* | (2006.01) | |
| *G16H 40/67* | (2018.01) | |

(52) U.S. Cl.
CPC .............. *G16H 20/13* (2018.01); *A61J 1/00* (2013.01); *G06F 21/31* (2013.01); *G16H 40/67* (2018.01); *A61J 2205/60* (2013.01)

(58) Field of Classification Search
CPC ........ G16H 20/13; G16H 40/67; G06F 21/31; A61J 1/00; A61J 2205/60
See application file for complete search history.

(56) References Cited

U.S. PATENT DOCUMENTS

| | | | |
|---|---|---|---|
| 7,243,002 B1 * | 7/2007 | Hoganson .............. | G05B 11/44 700/215 |
| 8,116,906 B2 * | 2/2012 | Valerino, Sr. .......... | G06Q 50/30 700/229 |
| 9,352,914 B2 * | 5/2016 | Le .......................... | B65G 51/32 |
| 9,539,178 B1 * | 1/2017 | Valerino, Sr. .......... | G07F 9/001 |
| 9,592,969 B2 * | 3/2017 | Wolfe ..................... | B65G 51/44 |
| 9,821,965 B2 * | 11/2017 | Wolfe ..................... | B65G 51/44 |
| 10,023,402 B2 | 7/2018 | Hoganson et al. | |
| 10,867,457 B1 * | 12/2020 | McCracken, Jr. ... | G06K 7/1413 |
| 2006/0202824 A1 * | 9/2006 | Carroll .................. | G09F 3/0376 340/568.1 |
| 2014/0048593 A1 * | 2/2014 | Hoganson .............. | G16H 40/67 206/459.5 |
| 2014/0330428 A1 * | 11/2014 | Wolfe ..................... | B65G 51/44 700/226 |

(Continued)

*Primary Examiner* — Michael Collins
(74) *Attorney, Agent, or Firm* — Allen, Dyer, Doppelt + Gilchrist, P.A. Attorney at Law (57) ABSTRACT

A pharmaceutical transport system may include an authentication server for storing authorized user identifications (IDs), and a pharmaceutical transport device movable within a pneumatic network. The transport device may include a container, a radio frequency identification (RFID) reader configured to obtain a user identification (ID) based upon a user RFID transmitter being presented adjacent thereto, and wireless communications circuitry to wirelessly communicate the obtained user ID to the authentication server. The pharmaceutical transport device may also include an electronic lock configured to unlock the container responsive to an unlock command via the wireless communications circuitry and from the authentication server based upon a match between the obtained user ID and one of the plurality of authorized user IDs.

21 Claims, 11 Drawing Sheets

(56) References Cited

U.S. PATENT DOCUMENTS

| | | | |
|---|---|---|---|
| 2016/0042582 A1* | 2/2016 | Hyde | E05B 67/22 |
| | | | 70/53 |
| 2016/0096691 A1* | 4/2016 | Gross | B65G 51/46 |
| | | | 406/10 |
| 2019/0183737 A1* | 6/2019 | Valerino, Sr. | B65G 51/26 |

* cited by examiner

PHARMACEUTICAL TRANSPORT SYSTEM INCLUDING RFID BASED LOCK OPERATION AND RELATED METHODS

TECHNICAL FIELD

The present invention relates to the field of pneumatic transport systems, and, more particularly, to containers for pneumatic transport systems and related methods.

BACKGROUND

A pneumatic transport system is a system that propels containers, typically cylindrical in shape, through networks of tubes by compressed air or by partial vacuum. Solid objects may be placed in a container and transported relatively easily through a pneumatic transport system.

One implementation for a pneumatic transport system may be in health care. For example, a hospital may have a pneumatic transport system to distribute pharmaceuticals. In some instances, for example, where controlled pharmaceuticals are distributed, the system may include one or more security features to restrict access to the controlled pharmaceuticals. For example, a lock may be used to restrict access to within the container.

U.S. Pat. No. 9,592,969 to Wolfe et al. is directed to a system for locking a carrier container. Wolfe et al. discloses identifying an authorized person (e.g., user ID) by, for example, by barcodes and barcode readers, magnetic card/stripe readers, RFID tags/readers, NFC tags/readers, other wireless technologies, PIN codes, biometric identification, and/or any other suitable means. If access control of the contents is not required, then no authentication step is performed. However, even if authentication is not required, the user ID can still be used to track the individual(s) who accessed the container and the content within. If access control is required, then the carrier ID and/or item(s) ID and the user ID are used to determine if the identified user is authorized to gain access to the container.

U.S. Pat. No. 10,023,402 to Hoganson et al. is directed to a system for carrier identification in a pneumatic tube system. More particularly, Hoganson et al. discloses a system that provides for the identification and monitoring of carriers within a pneumatic carrier system. Each carrier which is to be employed within the system includes an identification device such as a radio frequency identification (RFID) chip which has stored thereon identification information for the carrier. Positioned throughout the system are communications devices such as antennas and readers which are employed to read and/or write identification information on the chip. When a carrier is put in the system, a destination location can be associated with the particular carrier ID. This associated information is then employed to, among many things, monitor and confirm identity of the carrier as it moves to its destination.

SUMMARY

A pharmaceutical transport system may include an authentication server configured to store a plurality of authorized user identifications (IDs) and a pneumatic network. The pharmaceutical transport system may also include a pharmaceutical transport device movable within the pneumatic network. The pharmaceutical transport device may include a container, such as for receiving at least one pharmaceutical therein, and a radio frequency identification (RFID) reader carried by the container and configured to obtain a user identification (ID) based upon a user RFID being transmitter presented adjacent thereto.

The pharmaceutical transport device may also include wireless communications circuitry configured to wirelessly communicate the obtained user ID to the authentication server, and an electronic lock. The electronic lock may be configured to unlock the container responsive to an unlock command via the wireless communications circuitry and from the authentication server based upon a match between the obtained user ID and one of the plurality of authorized user IDs The container may have a given container ID associated therewith. The wireless communications circuitry may be configured to wirelessly communicate the given container ID to the authentication server, for example.

Selected ones of the plurality of authorized user IDs may be associated with the given container ID. The authentication server may be configured to generate and communicate the unlock command based upon a match between the obtained user ID and the one of the plurality of stored authorized user IDs for the given container ID, for example.

The container may include a tubular body, and a pair of movable end caps coupled to respective ends of the tubular body; and the electronic lock may secure at least one of the tubular end caps to the tubular body, for example. The tubular body may include a pair of mating container sections.

The electronic lock may include a processor and associated memory, and an electromechanical actuator coupled to the processor. The wireless communications circuitry and the RFID reader may be coupled to the processor.

The wireless communications circuitry may include WiFi wireless communications circuitry, for example. The RFID transmitter may include a passive RFID transmitter. The RFID reader may be configured to obtain the user ID based upon an ID token being presented adjacent thereto. The ID token may include a body and the RFID transmitter carried by the body.

A method aspect is directed to securing a pharmaceutical transport device movable within a pneumatic network, the pharmaceutical transport device comprising a container, a radio frequency identification (RFID) reader, and an electronic lock. The method may comprise obtaining a user identification (ID) based upon a user RFID transmitter being presented adjacent the RFID reader, and wirelessly communicating the obtained user ID to an authentication server using the wireless communications circuitry. In addition, the method may include operating the electronic lock to unlock the container responsive to an unlock command via the wireless communications circuitry and from the authentication server based upon a match between the obtained user ID and one of a plurality of authorized user IDs.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Referring initially to FIGS. 1-4, a pharmaceutical transport system 20 includes a pneumatic network 21. More particularly, the pneumatic network 21 includes at least one tube 22 to permit the transport of pharmaceuticals 27 between endpoints 23, 24 based upon the movement of air, for example, from a blower. The pneumatic network 21 may extend throughout a facility, for example, a hospital, to permit transport of the pharmaceuticals throughout the hospital, for example, from a pharmacy to another part of the hospital.

The pharmaceutical transport system 20 also includes a pharmaceutical transport device 30 that is movable within the pneumatic network 21. For example, the pharmaceuticals 27 are typically transported through the pneumatic network 21 within the pharmaceutical transport device 30. The pharmaceutical transport device 30 includes a container 31, for example, having a tubular shape, and having open and closed positions for receiving at least one pharmaceutical 27 therein. While a pharmaceutical is described herein, it should be appreciated by those skilled in that art that a pharmaceutical may include prescription and non-prescription medication, controlled substances, biological samples, and/or controlled medical devices.

The container 31 includes a tubular body 32 and a pair of movable end caps 33a, 33b coupled to respective ends 34a, 34b of the tubular body. While the movable end caps 33a, 33b are illustratively hingedly coupled to the tubular body 32, those skilled in the art will appreciate that one or both of the end caps 33a, 33b may be fully removable.

The pharmaceutical transport device 30 also includes a radio frequency identification (RFID) reader 45. The RFID reader 45 is carried by the container 31.

The pharmaceutical transport device 30 includes wireless communications circuitry 60 coupled the RFID reader 45 and carried by the container 31. The wireless communications circuitry 60 may include WiFi wireless communications circuitry, for example. Of course, the wireless communications circuitry 60 may include other and/or additional wireless circuitry, for example, near-field communications (NFC) circuitry, Bluetooth circuitry, etc.

The pharmaceutical transport device 30 also includes an electronic lock 40 coupled to the wireless communications circuitry 60 and locking the container 31 in the closed position. More particularly, the electronic lock 40 secures the movable end caps 33a, 33b to the tubular body 32 in the closed position.

Figure 1:
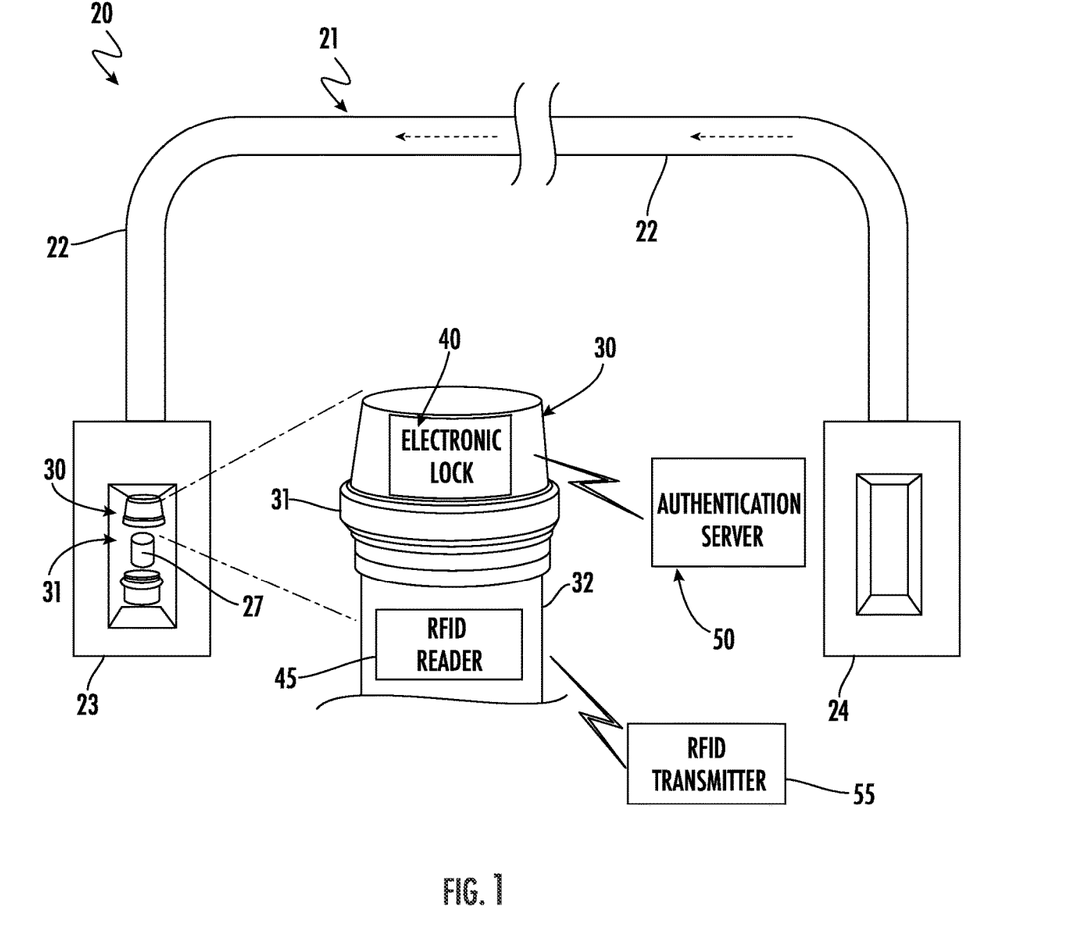
FIG. 1 is a schematic diagram of a pharmaceutical transport system in accordance with an embodiment.
Figure 2:
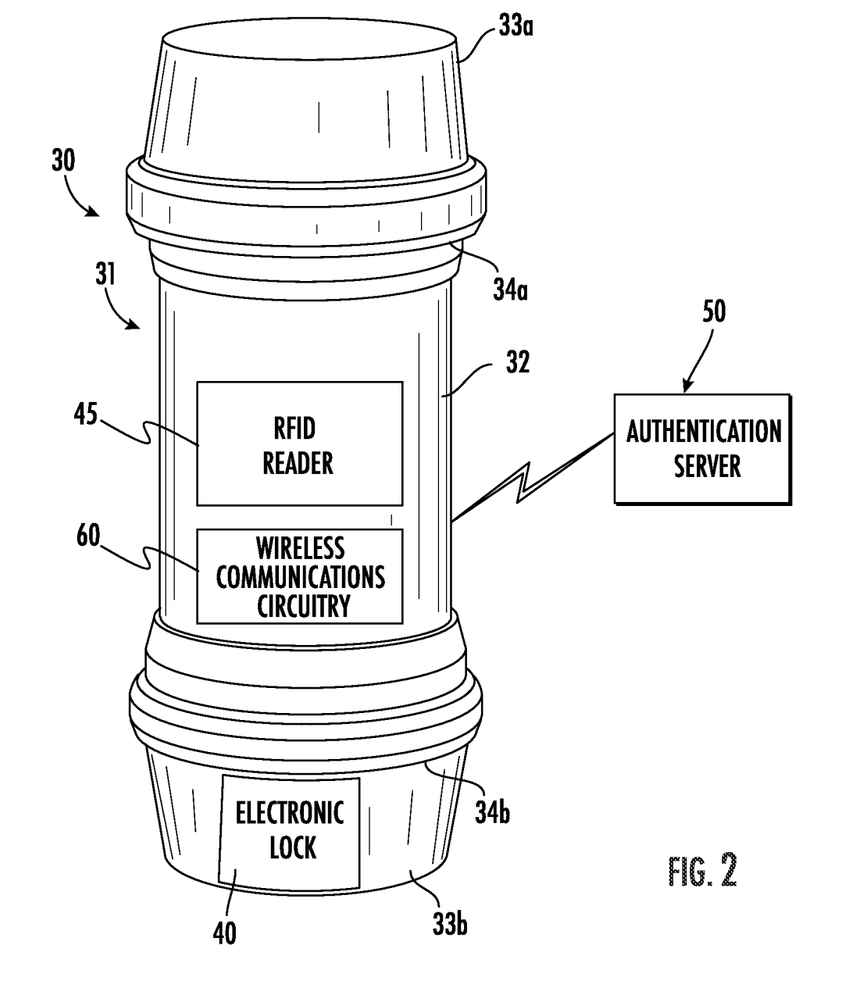
FIG. 2 is a schematic diagram of a portion of the pharmaceutical transport system of FIG. 1.
Figure 3:
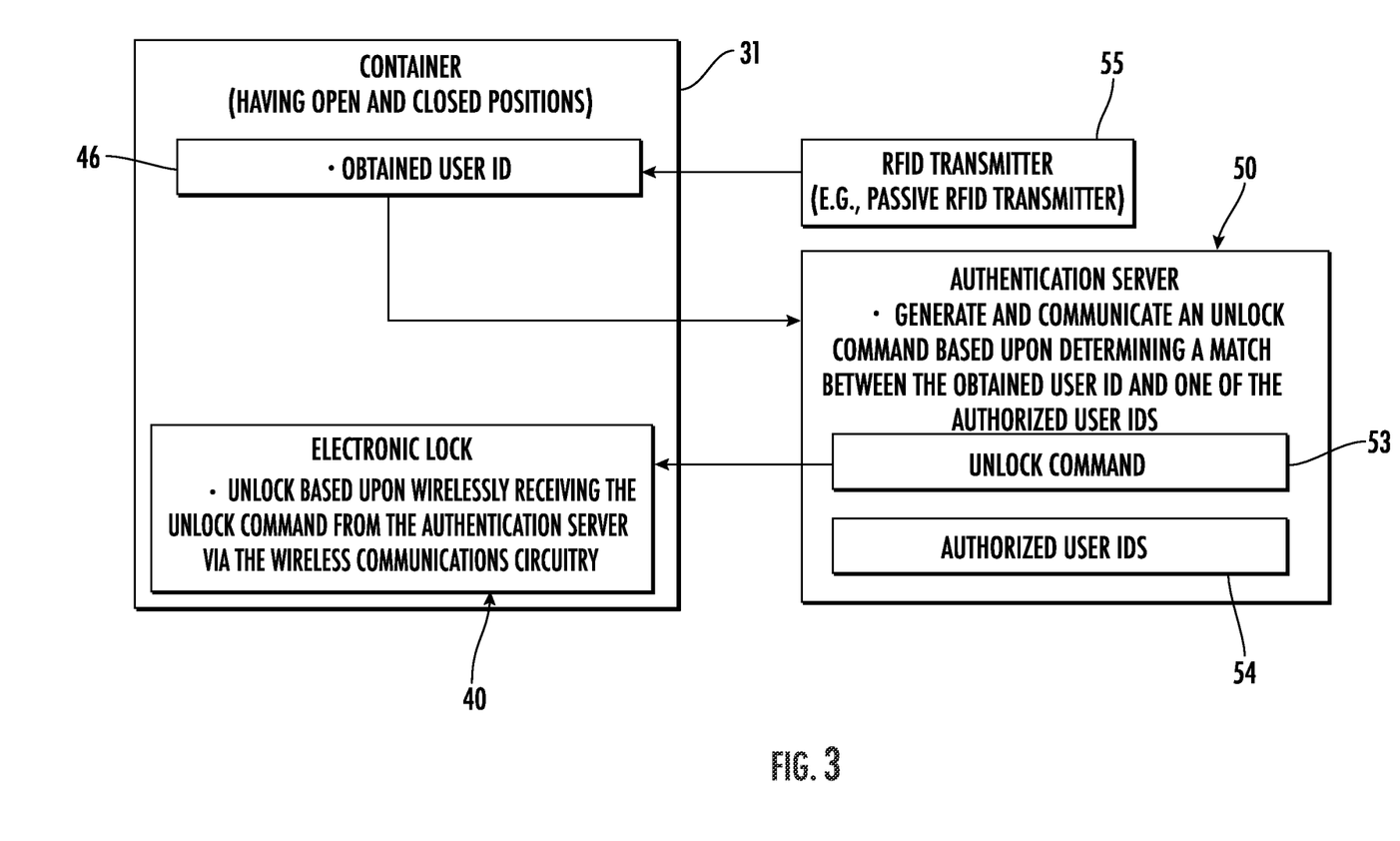
FIG. 3 is a schematic block diagram illustrating operation of pharmaceutical transport system of FIG. 1.
Figure 4:
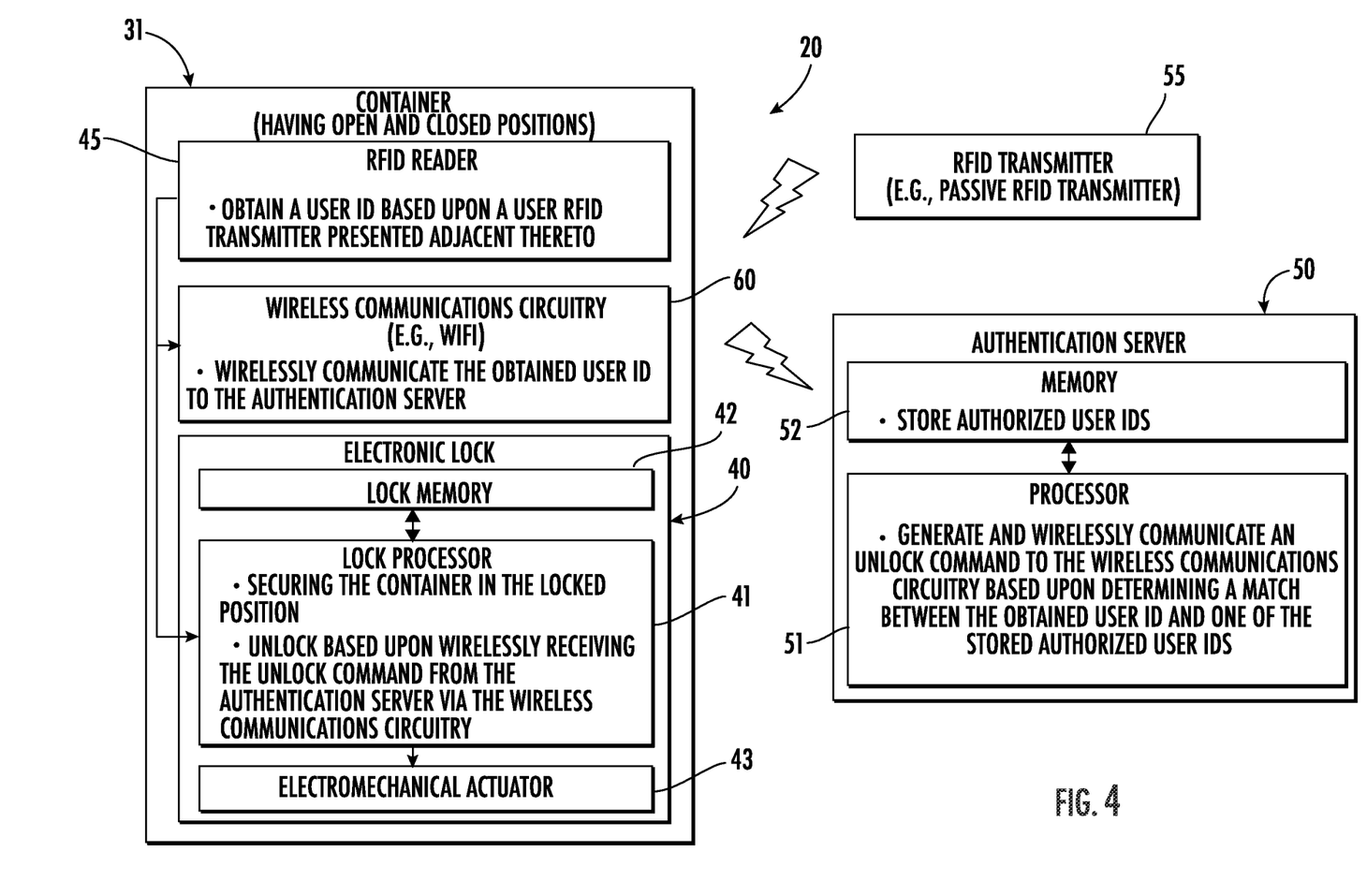
FIG. 4 is a schematic block diagram of the pharmaceutical transport system of FIG. 1.

The electronic lock 40 includes a lock processor 41 and an associated lock memory 42 (FIG. 4). The wireless communications circuitry 60 and the RFID reader 45 may be coupled to the lock processor 41. An electromechanical actuator 43 is coupled to the lock processor 41. While one electronic lock 40 is illustrated, those skilled in the art will appreciate that the electronic lock may include more than one electromechanical actuator 43, for example, corresponding to each of the movable end caps 33a, 33b (e.g., and with a shared processor 41). Of course, other elements of the electronic lock 40 may be shared or there may be two or more physically separated electronic locks.

The pharmaceutical transport system 20 also includes an authentication server 50 that includes a server processor 51 and associated memory 52. The authentication server 50 stores authorized user IDs 54 in the memory 52. The authentication server 50 generates and wirelessly communicates an unlock command 53 to the wireless communications circuitry 60, as will be described herein. While operations of the electronic lock 40 and authentication server 50 are described herein, it will be appreciated by those skilled in the art that the operations are performed based upon cooperation between the respective processors 41, 51 and respective memories 42, 52.

Figure 5:
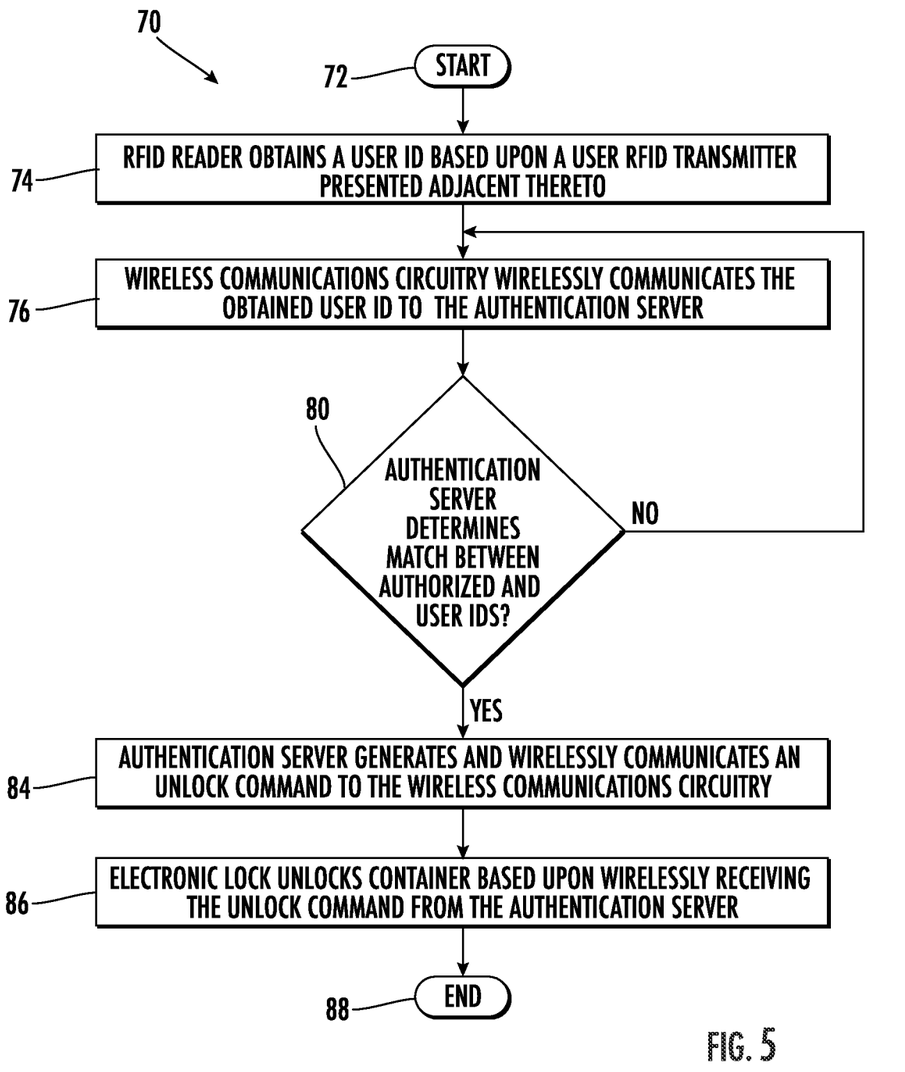
FIG. 5 is a flow diagram illustrating operation of the pharmaceutical transport system of FIG. 1.

Referring now to the flowchart 70 in FIG. 5, beginning at Block 72, authentication operations will now be described. At Block 74, the RFID reader 45 obtains a user ID 46, for example, from a given user, based upon a user RFID transmitter 55 presented adjacent the RFID reader. The RFID transmitter 55 may be a passive RFID transmitter, for example.

Figure 6:
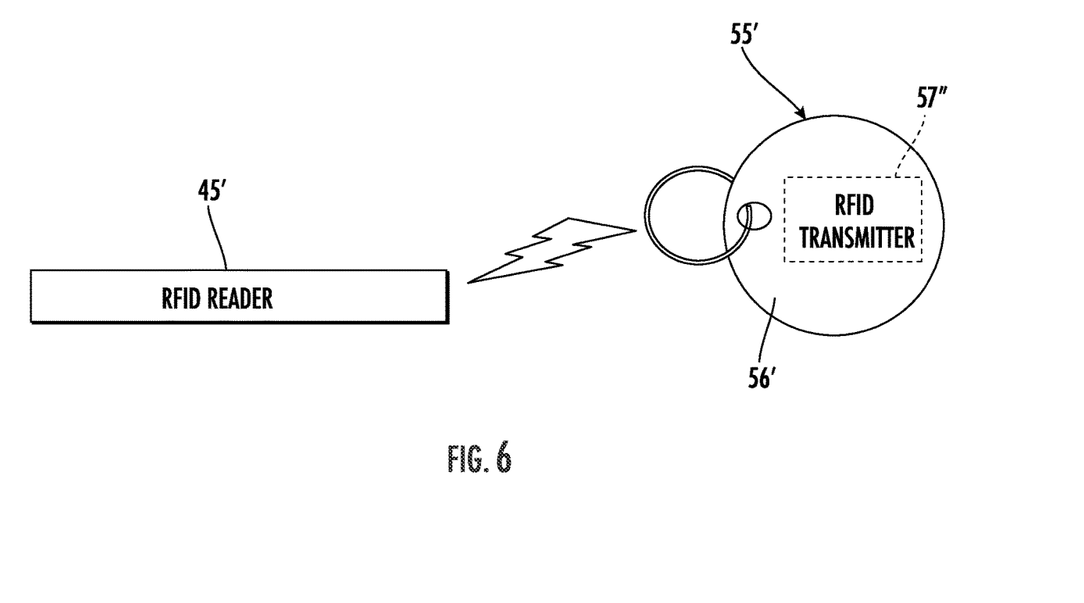
FIG. 6 is a schematic diagram an RFID transmitter for operation with an RFID reader of a pharmaceutical transport system in accordance with an embodiment.

Referring briefly to FIG. 6, in another embodiment, the RFID reader 45' may obtain the user ID based upon an ID token 55' being presented adjacent the RFID reader. The ID token 55' may include a body 56' and an RFID transmitter 57' carried by the body.

At Block 76, the wireless communications circuitry 60 wirelessly communicates the obtained user ID 46 to the authentication server 50. The authentication server 50, at Block 80, determines a match between the obtained user ID 46 and one of the stored authorized user IDs 54. If, at Block 80 there is a match between the obtained user ID 46 and one of the stored authorized user IDs 54, the authentication server 50 generates and wirelessly communicates an unlock command 53 to the wireless communications circuitry 60 (Block 84). At Block 86, for example, upon receipt of the unlock command 53 from the authentication server 50 via the wireless communications circuitry 60, the electronic lock 40 unlocks the container 31.

If, at Block 80, the authentication server 50 determines that that there is no match between the obtained user ID 46 and one of the stored IDs 54, the authentication server polls for receipt of another user ID for comparison or matching. Operations end at Block 88.

Figure 7:
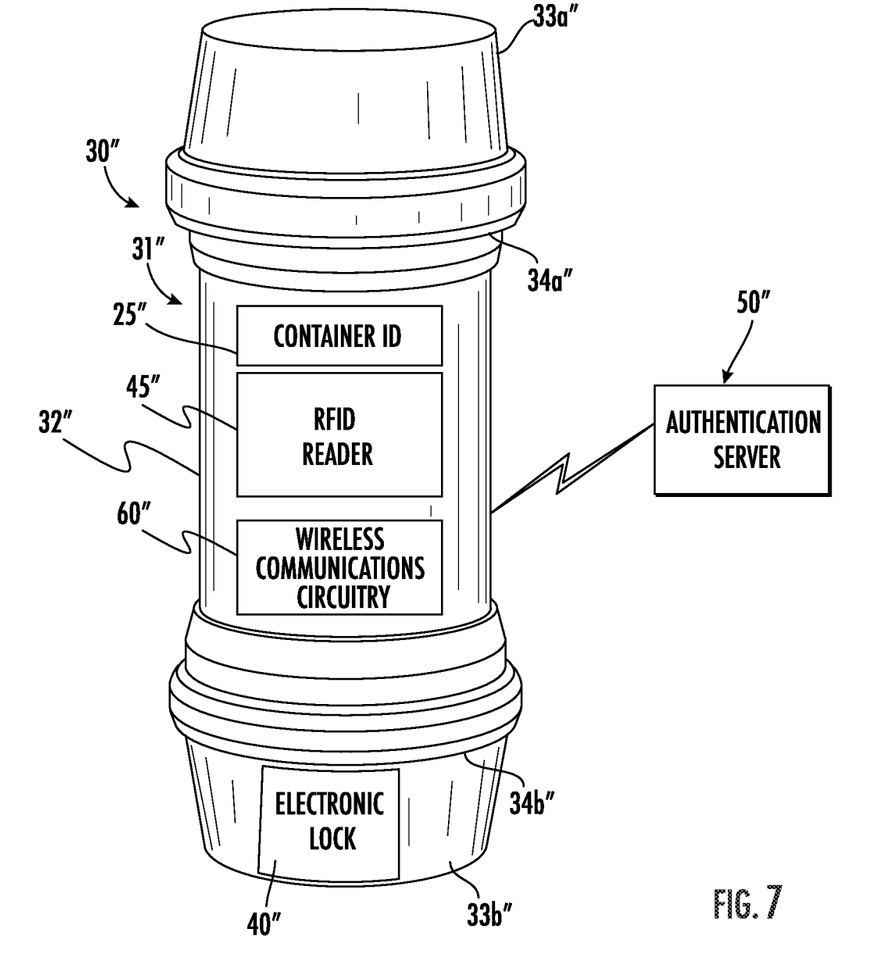
FIG. 7 is a schematic diagram of a portion of a pharmaceutical transport system in accordance with an embodiment.
Figure 8:
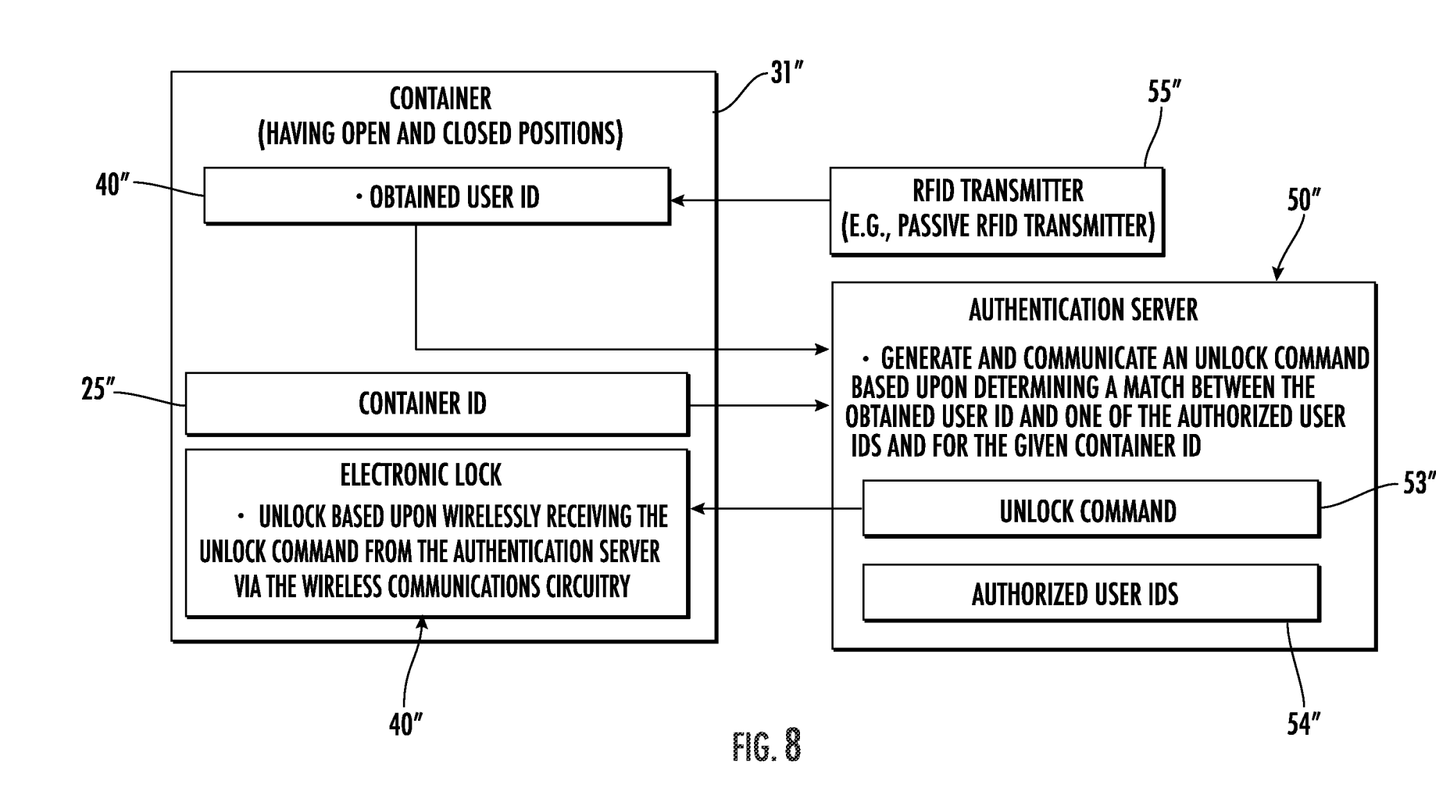
FIG. 8 is a schematic block diagram illustrating operation of pharmaceutical transport system in accordance with the embodiment of FIG. 7.
Figure 9:
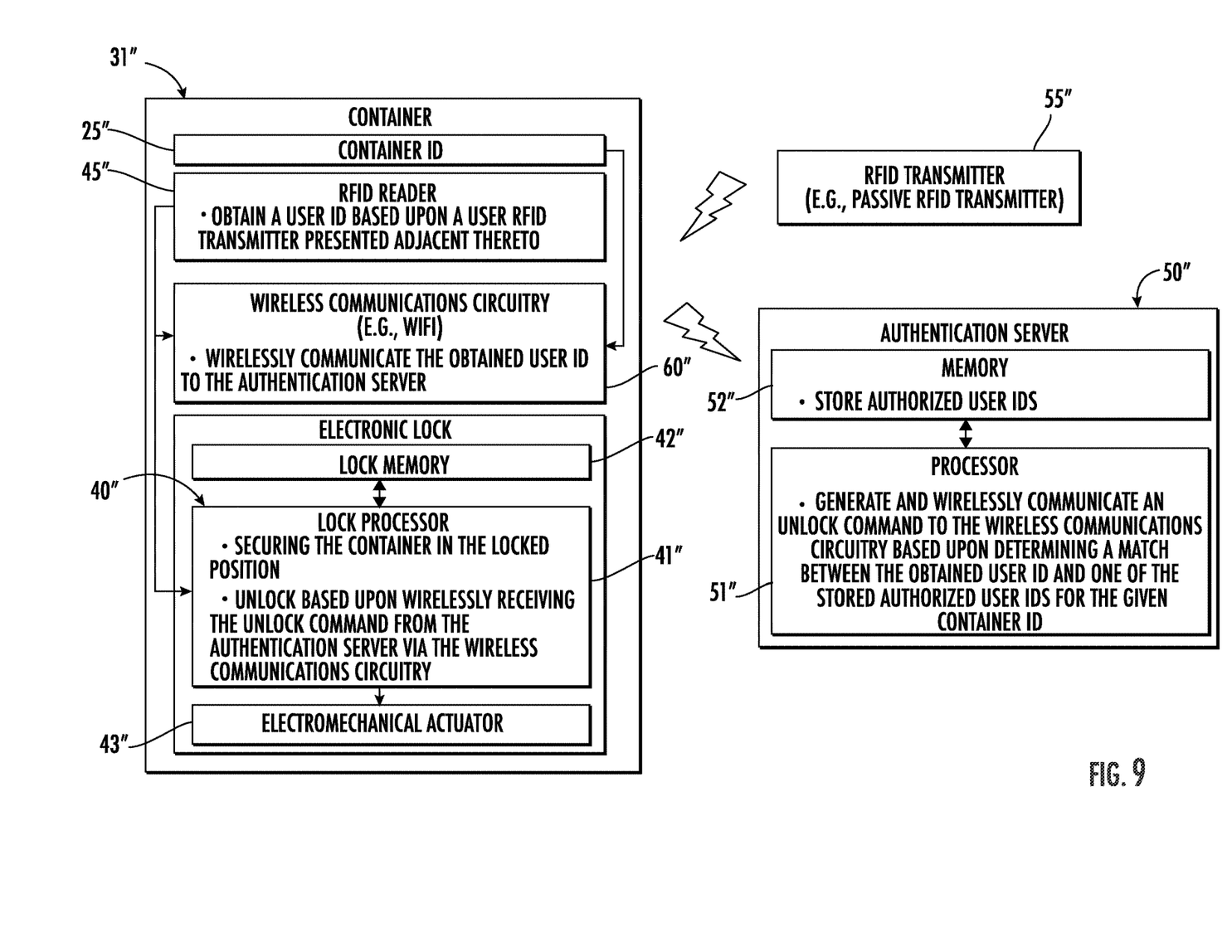
FIG. 9 is a schematic block diagram of the pharmaceutical transport system in accordance with the embodiment of FIG. 7.
Figure 10:
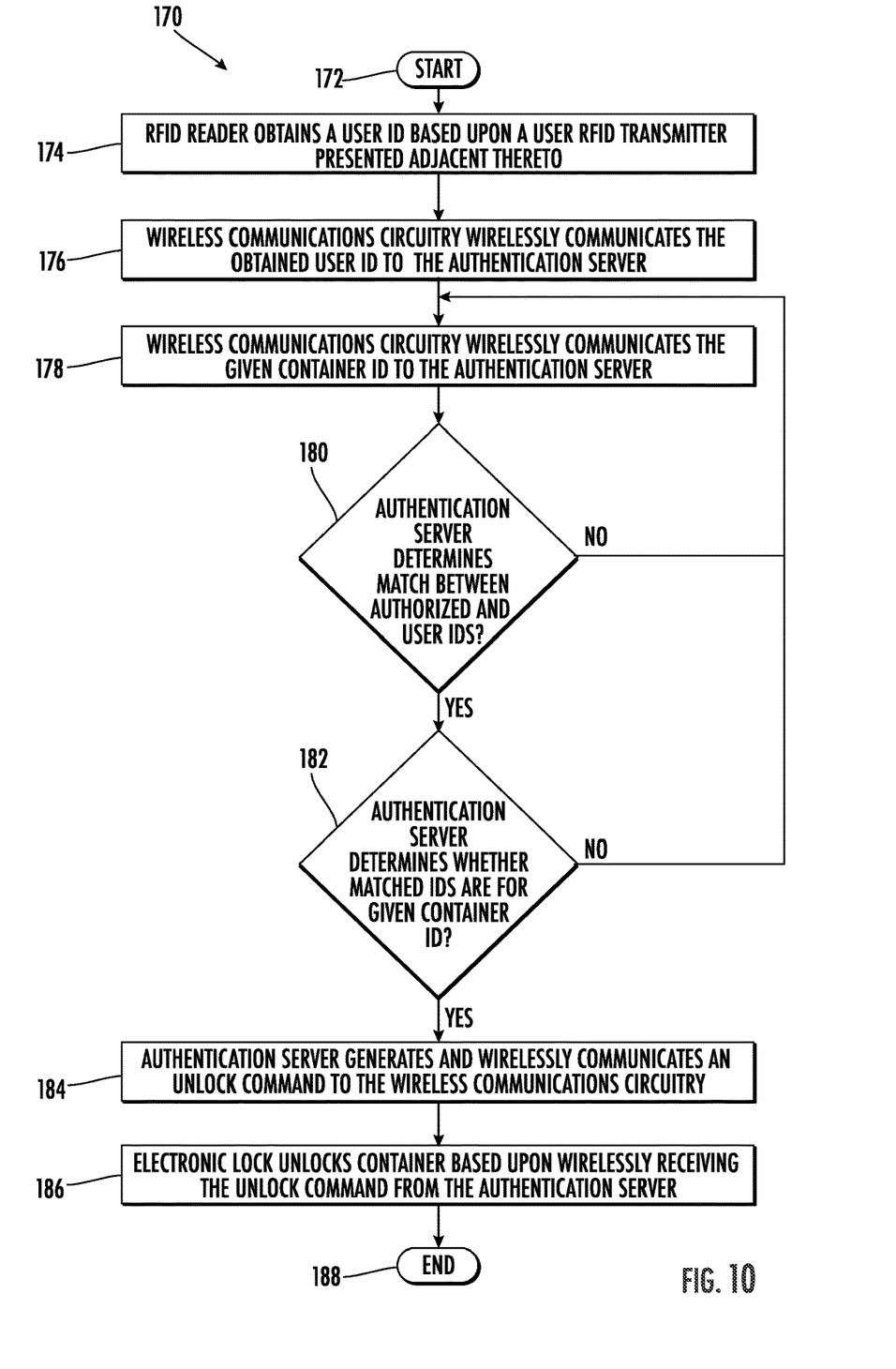
FIG. 10 is a flow diagram illustrating operation of the pharmaceutical transport system in accordance with the embodiment of FIG. 7.

Referring now to FIGS. 7-9, and the flowchart 170 in FIG. 10, beginning at Block 172, authentication operations according to another embodiment will now be described. The pharmaceutical transport device 30" (container 31") has a given container identifier (ID) 25" associated therewith. The container ID 25" is in the form of a digital code and uniquely identifies that container, for example, within the pneumatic network.

At Block 174, the RFID reader 45" obtains a user ID 46", for example, from a given user, based upon a user RFID transmitter 55" being presented adjacent the RFID reader. At Block 176, the wireless communications circuitry 60" wirelessly communicates the obtained user ID 46" to the authentication server 50'. At Block 178 the wireless communications circuitry 60" communicates the given container ID 25" to the authentication server 50". Selected ones of the authorized user IDs 54" are associated with the given container ID 25", for example, as may be the case when multiple users are authorized to open a given container or set of containers.

The authentication server 50", at Block 180, determines a match between the obtained user ID 46" and one of the stored authorized user IDs 54". If, at Block 180 there is a match between the obtained user ID 46" and one of the stored authorized user IDs 54", the authentication server 50' determines whether the matched obtained user ID 46" and one of the stored authorized user IDs 54" are for the given container ID 25" (Block 182). If at Block 182, there is a match between the obtained user ID 46" and one of the stored authorized user IDs 54" for the given container ID 25", the authentication server 50" generates and wirelessly communicates an unlock command 53" to the wireless communications circuitry 60" (Block 184). At Block 186, for example, upon receipt of the unlock command 53" from the authentication server 50" via the wireless communications circuitry 60", the electronic lock 40" unlocks container 31".

If the authentication server 50" determines that that there is no match between the obtained user ID 46" and one of the stored IDs 54" (Block 180), or there is no match between the obtained user ID 46" and one of the stored authorized user IDs 54" for the given container ID 25" (Block 182), the authentication server 50" polls for receipt of another user ID for comparison or matching. Operations end at Block 188. Elements illustrated in FIGS. 7-10, but not specifically described are similar the elements described with respect to embodiments illustrated in FIGS. 1-5.

Figure 11:
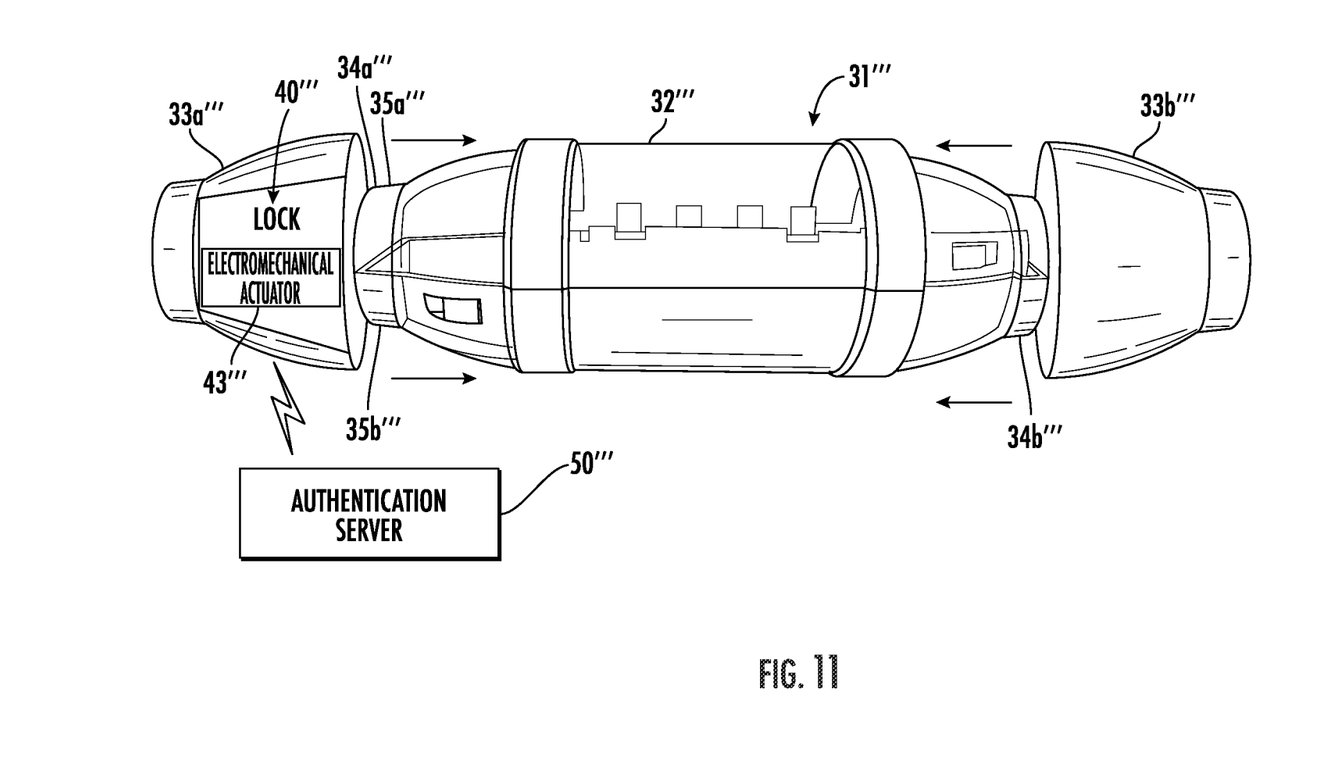
FIG. 11 is a schematic diagram of a portion of a pharmaceutical transport system in accordance with another embodiment.

Referring now to FIG. 11, in another embodiment, the tubular body 32''' includes a pair of mating container sections 35a''', 35b''', for example, in a clam-shell configuration and has a generally prolate spheroid shape (e.g., a football shape). End caps 33a''', 33b''' couple over respective ends 34a''', 34b''' of the tubular body 32'''. The electronic lock 40''' illustratively secures one of the end caps 33a''', 33b''' over the ends of the pair of mating container sections 35a''', 35b'''. The electromechanical actuator 43''' may extend into or couple to the ends 34a''', 34b''' to secure the container 31''' in the closed position. The electronic lock 40''', e.g., in the form of two physical electromechanical actuators, may secure both ends caps 33a''', 33b''' to the respective ends, and operate or open based up the unlock command from the authentication server 50'''.

A method aspect is directed to a security method in a pharmaceutical transport system 20 that includes an authentication server 50 configured to store a plurality of authorized user identifications (IDs) 54, a pneumatic network 21, and a pharmaceutical transport device 30 movable within the pneumatic network. The method includes obtaining a user identification (ID) 46 based upon a user radio frequency identification (RFID) transmitter 55 being presented adjacent an RFID reader 45 carried by a container 31. The method also includes wirelessly communicating the obtained user ID 46 to the authentication server 50 using wireless communications circuitry 60 coupled to the RFID reader 45 and carried by the container 31 and configured to wirelessly communicate the obtained user ID to the authentication server. The method further includes operating an electronic lock 40 coupled to the wireless communications circuitry 60 and unlocking the container based upon wirelessly receiving an unlock command 53 generated by and communicated from the authentication server 50 via the wireless communications circuitry. The authentication server 50 may be configured to generate and wirelessly communicate the unlock command 53 to the wireless communications circuitry 60 based upon determining a match between the obtained user ID and one of the plurality of stored authorized user IDs.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A pharmaceutical transport system comprising:
an authentication server configured to store a plurality of authorized user identifications (IDs); and
a pharmaceutical transport device movable within a pneumatic network and comprising
a container,
a radio frequency identification (RFID) reader carried by the container and configured to obtain a user identification (ID) based upon a user RFID transmitter being presented adjacent thereto,
wireless communications circuitry carried by the container and configured to wirelessly communicate the obtained user ID to the authentication server, and
an electronic lock configured to unlock the container responsive to an unlock command via said wireless communications circuitry and from the authentication server based upon a match between the obtained user ID and one of the plurality of authorized user IDs.

2. The pharmaceutical transport system of claim 1 wherein said container has a given container ID associated therewith; and wherein said wireless communications circuitry is configured to wirelessly communicate the given container ID to said authentication server.

3. The pharmaceutical transport system of claim 2 wherein selected ones of the plurality of authorized user IDs are associated with the given container ID; and wherein said authentication server is configured to generate and communicate the unlock command further based upon a match between the obtained user ID and the one of the plurality of authorized user IDs for the given container ID.

4. The pharmaceutical transport system of claim 1 wherein the container comprises a tubular body, and a pair of movable end caps coupled to respective ends of the tubular body; and wherein the electronic lock secures at least one of the tubular end caps to the tubular body.

5. The pharmaceutical transport system of claim 4 wherein the tubular body comprises a pair of mating container sections.

6. The pharmaceutical transport system of claim 1 wherein the electronic lock comprises a processor and associated memory, and an electromechanical actuator coupled to the processor.

7. The pharmaceutical transport system of claim 6 wherein said wireless communications circuitry and said RFID reader are coupled to said processor.

8. The pharmaceutical transport system of claim 1 wherein the wireless communications circuitry comprises WiFi wireless communications circuitry.

9. The pharmaceutical transport system of claim 1 wherein the RFID transmitter comprises a passive RFID transmitter.

10. The pharmaceutical transport system of claim 1 wherein said RFID reader is configured to obtain the user ID based upon an ID token being presented adjacent thereto, the ID token comprising a body and the RFID transmitter carried by the body.

11. A pharmaceutical transport device movable within a pneumatic network comprising:
 a container;
 a radio frequency identification (RFID) reader carried by the container and configured to obtain a user identification (ID) based upon a user RFID transmitter being presented adjacent thereto;
 wireless communications circuitry carried by the container and configured to wirelessly communicate the obtained user ID to an authentication server; and
 an electronic lock configured to unlock the container responsive to an unlock command via said wireless communications circuitry and from the authentication server based upon a match between the obtained user ID and one of the plurality of authorized user IDs.

12. The pharmaceutical transport device of claim 11 wherein the container has a given container ID associated therewith; and wherein said wireless communications circuitry is configured to wirelessly communicate the given container ID to the authentication server.

13. The pharmaceutical transport device of claim 11 wherein the container comprises a tubular body, and a pair of movable end caps coupled to respective ends of the tubular body; and wherein said electronic lock secures at least one of the tubular end caps to the tubular body.

14. The pharmaceutical transport device of claim 13 wherein said tubular body comprises a pair of mating container sections.

15. The pharmaceutical transport device of claim 11 wherein the electronic lock comprises a processor and associated memory, and an electromechanical actuator coupled to the processor.

16. A method of securing a pharmaceutical transport device movable within a pneumatic network, the pharmaceutical transport device comprising a container, a radio frequency identification (RFID) reader carried by the container, and an electronic lock, the method comprising:
 obtaining a user identification (ID) based upon a user RFID transmitter being presented adjacent the RFID reader;
 wirelessly communicating the obtained user ID to an authentication server using wireless communications circuitry carried by the container; and
 operating the electronic lock to unlock the container responsive to an unlock command via the wireless communications circuitry and from the authentication server based upon a match between the obtained user ID and one of a plurality of authorized user IDs.

17. The method of claim 16 wherein the container has a given container ID associated therewith; and comprising using the wireless communications circuitry to wirelessly communicate the given container ID to the authentication server.

18. The method of claim 17 wherein selected ones of the plurality of authorized user IDs are associated with the given container ID; and wherein the wireless communications circuitry obtains the unlock command from the authentication server further based upon a match between the obtained user ID and the one of the plurality of stored authorized user IDs for the given container ID.

19. The method of claim 16 wherein the electronic lock comprises a processor and associated memory, and an electromechanical actuator coupled to the processor.

20. The method of claim 19 wherein the wireless communications circuitry and the RFID reader are coupled to the processor.

21. The method of claim 16 wherein the RFID reader obtains the user ID based upon an ID token being presented adjacent thereto, the ID token comprising a body and the RFID transmitter carried by the body.

\* \* \* \* \*